(12) United States Patent
Stokes et al.

(10) Patent No.: US 8,197,504 B2
(45) Date of Patent: Jun. 12, 2012

(54) SAFE TISSUE PUNCTURE DEVICE

(75) Inventors: Michael J. Stokes, Cincinnati, OH (US); Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 477 days.

(21) Appl. No.: 12/113,758

(22) Filed: May 1, 2008

(65) Prior Publication Data
US 2009/0275967 A1   Nov. 5, 2009

(51) Int. Cl.
*A61B 17/34* (2006.01)
(52) U.S. Cl. .................................................. 606/185
(58) Field of Classification Search .......... 606/139, 606/142, 143, 151, 167, 172, 205–209
See application file for complete search history.

(56) References Cited

U.S. PATENT DOCUMENTS

| | | | | |
|---|---|---|---|---|
| 4,807,625 A | * | 2/1989 | Singleton | 606/125 |
| 5,762,070 A | * | 6/1998 | Nagamatsu | 600/564 |
| 2004/0087831 A1 | | 5/2004 | Michels et al. | |
| 2004/0143159 A1 | * | 7/2004 | Wendlandt | 600/114 |
| 2005/0043758 A1 | * | 2/2005 | Golden et al. | 606/206 |
| 2005/0075653 A1 | * | 4/2005 | Saadat et al. | 606/139 |
| 2005/0124986 A1 | | 6/2005 | Brounstein et al. | |
| 2007/0043380 A1 | * | 2/2007 | Ortiz et al. | 606/108 |
| 2009/0247992 A1 | | 10/2009 | Shalon et al. | |

FOREIGN PATENT DOCUMENTS

| | | |
|---|---|---|
| EP | 1535580 | 6/2005 |
| WO | WO 2007120775 A2 * | 10/2007 |
| WO | WO 2008/023374 | 2/2008 |
| WO | WO2008/028126 | 3/2008 |

* cited by examiner

*Primary Examiner* — S. Thomas Hughes
*Assistant Examiner* — Katherine M Shi
(74) *Attorney, Agent, or Firm* — Welsh Flaxman & Gitler LLC

(57) ABSTRACT

A method for safely penetrating the tissue of a gastric wall includes deploying a tissue puncture assembly including a suction device proximate the gastric wall tissue, applying a vacuum source to the suction device to draw a portion of the gastric wall tissue thereto and extending a needle through the portion of gastric wall tissue drawn into contact with the suction device. A device for safely penetrating the tissue of a gastric wall includes a tissue puncture assembly including a suction device in the form of a cup with suction ports therein and an open end. A needle is surrounded by the cup and extends through the cup toward the open end.

6 Claims, 3 Drawing Sheets

SAFE TISSUE PUNCTURE DEVICE

BACKGROUND OF THE INVENTION

1. Field of the Invention

The invention relates to a method and apparatus for gastric volume reduction. More particularly, the invention relates to methods and apparatuses for safely penetrating the gastric wall with a needle during gastric volume reduction procedures.

2. Description of the Related Art

Obesity is a medical condition affecting more than 30% of the population in the United States. Obesity affects an individual's personal quality of life and contributes significantly to morbidity and mortality. Obese patients, i.e., individuals having a body mass index ("BMI") greater than 30, often have a high risk of associated health problems (e.g., diabetes, hypertension and respiratory insufficiency), including early death. With this in mind, and as those skilled in the art will certainly appreciate, the monetary and physical costs associated with obesity are substantial. In fact, it is estimated the costs relating to obesity are in excess of 100 billion dollars in the United States alone. Studies have shown that conservative treatment with diet and exercise alone may be ineffective for reducing excess body weight in many patients.

Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure a small stomach pouch is separated from the remainder of the gastric cavity and attached to a resectioned portion of the small intestine. This resectioned portion of the small intestine is connected between the "smaller" gastric cavity and a distal section of small intestine allowing the passage of food therebetween. The conventional RYGB procedure requires a great deal of operative time. Because of the degree of invasiveness, post-operative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing a feeling of satiety. A band is placed around the stomach near the junction of the stomach and esophagus. The small upper stomach pouch is filled quickly, and slowly empties through the narrow outlet to produce the feeling of satiety. Other forms of bariatric surgery that have been developed to treat obesity include Fobi pouch, bilio-pancreatic diversion and gastroplasty or "stomach stapling".

Morbid obesity is defined as being greater than 100 pounds over one's ideal body weight. For individuals in this category, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss.

It is known to create cavity wall plications through endoscopic only procedures. However, operating solely within the interior of the gastric cavity limits the plication depth that can be achieved without cutting. Furthermore, access and visibility within the gastric and peritoneal cavities is limited in a purely endoscopic procedure as the extent of the reduction increases.

Endolumenal procedures, that is, transoral gastric restriction, often require acquisition of the lumen wall (that is, the gastric wall) in order to manipulate or cause effect to the tissue. When working within the lumen and penetrating from the mucosal layer to the serosal layer, it is a concern to potentially damage surrounding viscera due to lack of visibility. For gastric restriction, it is important to acquire the full gastric wall thickness for strength and durability of the procedure. The device will pass either a suture, loop or t-tag fastener through the full thickness of the gastric wall along the lesser curve to mimic a vertical banded gastroplaty procedure.

With the foregoing in mind, it is desirable to provide surgical weight loss procedures (and associated medical instruments) that are inexpensive, with few potential complications, and that provide patients with a weight loss benefit while buying time for the lifestyle changes necessary to maintain the weight loss. Further, it is desirable that the procedures and medical instruments be minimally invasive to the patient, allowing for a quick recovery and less scarring. The present invention provides such a procedure and medical instruments.

SUMMARY OF THE INVENTION

It is, therefore, an object of the present invention to provide a method for safely penetrating the tissue of a gastric wall. The method includes deploying tissue puncture assembly including a suction device proximate the gastric wall tissue, applying a vacuum source to the suction device to draw a portion of the gastric wall tissue thereto and extending a needle through the portion of gastric wall tissue drawn into contact with the suction device.

It is also an object of the present invention to provide a method wherein the vacuum source is pulsed to control the rate of tissue being drawn into the suction device.

It is another object of the present invention to provide a method wherein the suction device is in the form of a cup.

It is a further object of the present invention to provide a method wherein the cup has a first open configuration and a second closed configuration.

It is also an object of the present invention to provide a method wherein the suction device is in the form of a cup and the cup has a first open configuration and a second closed configuration.

It is another object of the present invention to provide a method wherein the cup of the suction device is deployed in its open configuration proximate the gastric wall tissue and the vacuum is applied as the cup of the suction device is moved into its closed configuration folding tissue therebetween.

It is a further object of the present invention to provide a method wherein the suction device includes ports on its inner surface and tissue is drawn into the suction device.

It is also an object of the present invention to provide a method wherein the suction device includes ports on its outer surface and tissue is drawn about the outer surface of the suction device.

It is another object of the present invention to provide a method wherein wherein the needle is an RF needle.

It is a further object of the present invention to provide a method wherein wherein the needle is a Veress needle.

It is also an object of the present invention to provide a device for safely penetrating the tissue of a gastric wall. The device includes a tissue puncture assembly having a suction device in the form of a cup with suction ports therein and an open end. A needle is surrounded by the cup and extends through the cup toward the open end.

It is another object of the present invention to provide a device wherein the suction device includes a first cup arm and a second cup arm pivot relative to one another so as to form the cup when in a closed configuration.

It is a further object of the present invention to provide a device wherein the first and second cup arms are mechanically pivoted.

It is also an object of the present invention to provide a device wherein the suction ports are on the inner surface of the cup such that tissue is drawn into the suction device.

It is another object of the present invention to provide a device wherein the suction ports are on the outer surface of the cup such that tissue is drawn about the suction device.

It is a further object of the present invention to provide a device wherein the needle is an RF needle.

It is also an object of the present invention to provide a device wherein the needle is a Veress needle.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Referring to the various figures, multiple embodiments of a deployment assembly for deploying various needles through the cavity wall of the gastric cavity are disclosed. Briefly, each of the deployment assemblies employ a combination needle and vacuum to achieve deployment of fastening elements in a desired manner. As will be appreciated based upon the following disclosure, the vacuum allows tissue to be suctioned to the needle rather than forcing the needle through the tissue for application of the fastening member.

Although the various embodiments of the present invention are designed for the application of various fasteners during gastric reduction surgery, it is contemplated the present invention may be utilized in a variety of surgical procedures without departing from the spirit of the present invention.

The various embodiments of the present deployment assembly are shaped and dimensioned for selective attachment to the distal end of a traditional endoscope. The gastric reduction apparatus is manipulated utilizing cable and suction available via the endoscope so as to position the deployment assembly at a desired orientation within the stomach. Although the present invention is adapted for attachment to the distal end of a endoscope, the present invention could be constructed with its own shaft without departing from the spirit of the invention.

Figure 1:
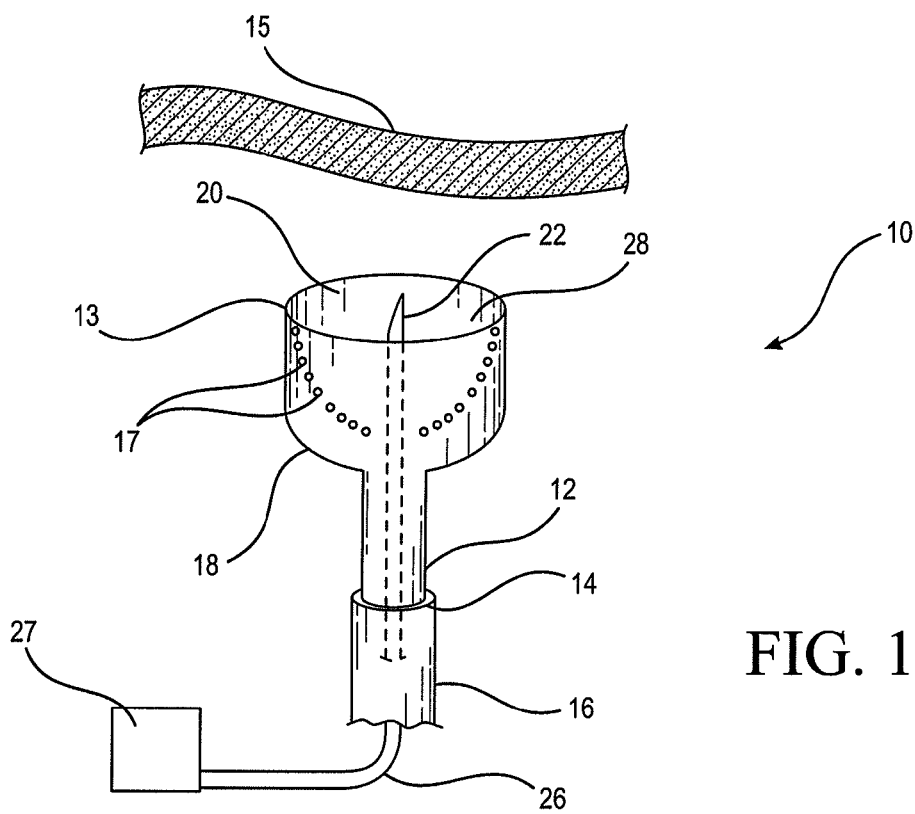
FIG. 1 is a perspective view of a tissue puncture assembly in accordance with a preferred embodiment of the present invention.
Figure 2:
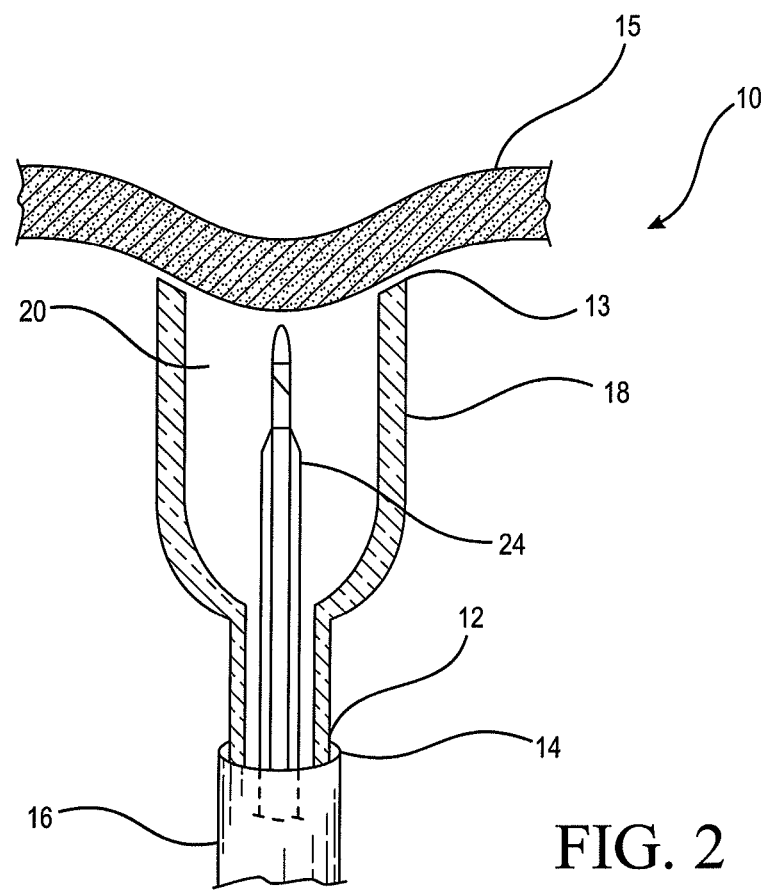
FIG. 2 is a cross sectional view of a tissue puncture assembly in use.

In particular, and with reference to the embodiment disclosed in FIGS. 1 and 2, the tissue puncture assembly 10 includes a proximal end 12 shaped and dimensioned for secure attachment to the distal end 14 of an endoscope 16. In accordance with a preferred embodiment, the proximal end 12 is secured to the endoscope 16 using conventional coupling elements, for example, a spring clamp or elastic sleeve, which those skilled in the art will fully appreciate.

The distal end 13 of the tissue puncture assembly 10 includes a suction cup 18 having a cavity 20 shaped and dimensioned for receiving tissue 15 in a manner discussed below in greater detail. The suction cup 18 is substantially bell shaped providing a wide open end 28 along the distal end 13 for receiving tissue for penetration with a needle 22, 24 while the tissue 15 is pulled within the suction cup 18 by suction ports 17. The needle 22, 24 is centrally positioned within the suction cup 18 for penetration of tissue 15 that is pulled within the suction cup 18.

The type of needle chosen to be used in the present tissue puncture assembly 10 may also assist in ensuring only desired layers of tissue come into contact with the needle 22. It is contemplated that one type of needle 22 which may be utilized in allowing full penetration of tissue without damaging the surrounding the viscera is a radio frequency needle 22. It is contemplated a user may employ a stationary hollow radiofrequency (RF) needle or a stationary solid radio frequency needle. As the tissue is drawn into contact with the radio frequency needle, the radio frequency energy assists in full thickness tissue penetration without damage to the outlying viscera. Another type of needle 22 which may be used is a regular needle 22. Using a stationary hollow or a stationary solid needle in combination with a vacuum assists in full thickness tissue penetration without damaging the outlying viscera. In accordance with yet a further embodiment, the needle may be a Veress needle 24. The Veress needle 24 has a retractable tip and a blunt end as seen in FIG. 2. A needle 24 of this type also assists in full thickness tissue penetration without damaging the outlying viscera. As will be appreciated based upon the following disclosure, the other embodiments disclosed herein may also employ needles as discussed above. The suction cup 18 is in fluid communication with a suction lumen 26 extending through the tissue puncture assembly 10 and the endoscope 16 for coupling with a suction source 27 located external of the patient. In accordance with a preferred embodiment of the present invention, tissue 15 is suctioned toward the needle 22, 24 in the following manner. The tissue is positioned adjacent the open end 28 of the suction cup 18 and pulses of vacuum are applied to the suction cup 18 for drawing tissue therein in a controlled step by step manner, thereby controlling the rate of tissue being drawn. As the tissue 15 is drawn within the suction cup 18, penetration of the needle 22, 24 into the tissue 15 is controlled via the various pulses of vacuum applied to the suction cup 18 and ultimately applied to draw the tissue within the suction cup 18. With each pulse, a certain amount of tissue 15 is pulled toward the needle 22, 24 allowing the needle 22, 24 to only penetrate that certain amount of tissue 15 vacuumed for that pulse. This process is repeated until the desired length of the needle 22, 24 has successfully penetrated the desired layers of tissue 15.

Figure 3:
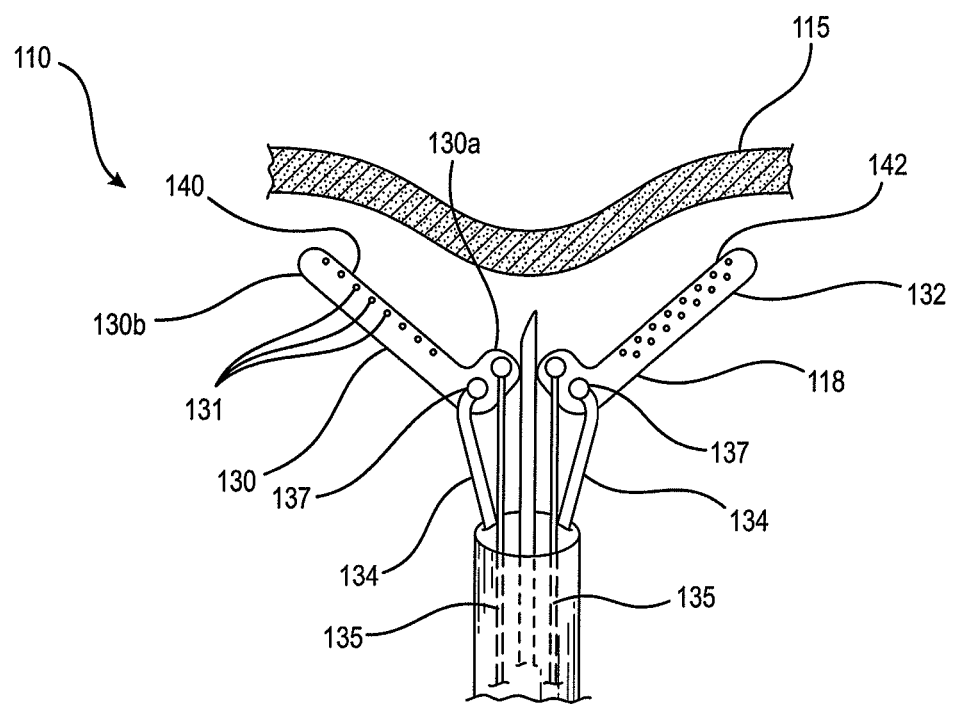
FIGS. 3 and 4 are cross sectional views of an alternate embodiment of a tissue puncture assembly in use.
Figure 4:
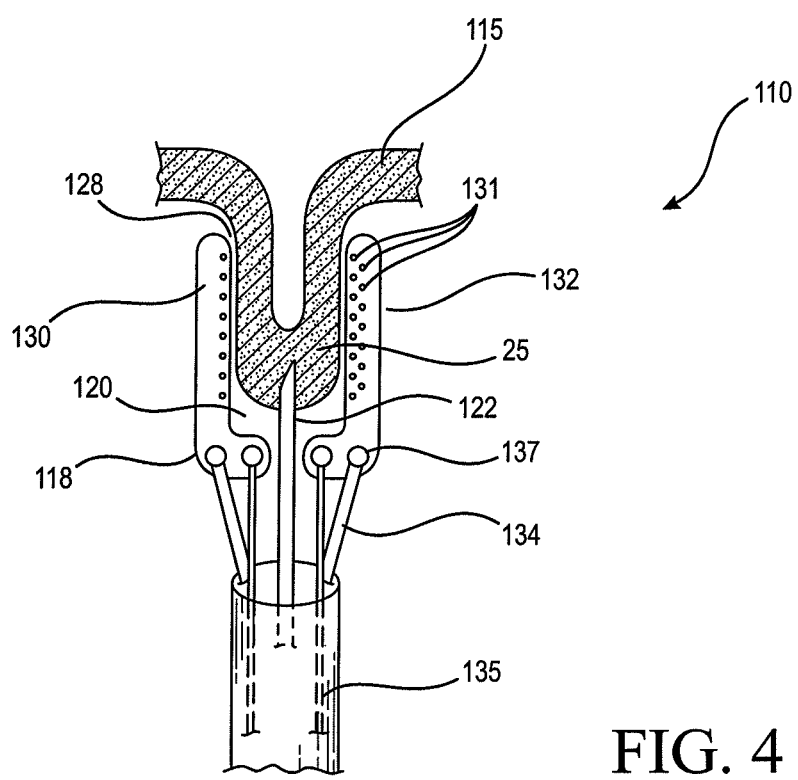

In accordance with an alternate embodiment, and with reference to FIGS. 3 and 4, the tissue puncture assembly 110 includes a suction cup 118 formed in two halves, that is, a first suction cup arm 130 and a second suction cup arm 132, which are pivotally secured to a support shaft 134. Therefore, when the suction cup arms 130, 132 are in their open configuration, as shown in FIG. 3, they have a greater surface area for attaching to tissue and when in a second closed configuration as shown in FIG. 4 form a cup with a cavity 120 and an open end 128.

When the first and second suction cup arms 130, 132 are brought together as discussed below they define a bell shaped section cup with a cavity 120 and a wide open end 128. The placement of the first suction cup arm 130 and the second suction cup arm 132 against the gastric cavity wall 115 when in their open configuration allows a larger expanse of tissue to grasped. As such a tissue fold 25 can be created and drawn within the space defined by the first suction cup arm 130 and the second suction cup arm 132 while the first and second suction cup arms 130, 132 are mechanically brought together creating a closed suction cup 118 with a cavity 120 and wide open end 128 similar to that presented above with regard to FIG. 1.

Each of the first and second suction cup arms 130, 132 is generally L-shaped (when viewed along a cross section as shown with reference to FIGS. 3 and 4) and when brought together form a closed U-shaped suction cup 118 (again when viewed along a cross section as shown with reference to FIG. 4). Each of the first and second suction cup members 130, 132 includes a series of suction ports 131 along their respective inner surfaces 140, 142 for drawing tissue therein.

In operation, suction is utilized to pull tissue 115 proximate to the first and second suction cup arms 130, 132 and into contact therewith via the series of suction ports 131 thereon. As such, the length of tissue 115 within the open suction cup 118 (that is, with the first and second suction cup arms extended apart as shown in FIG. 3) formed by opened first and second suction cup arms 130, 132 is folded as the suction continued to be applied and the first and second suction cup arms 130, 132 are forced together drawing the tissue 115 into a tissue fold 25 therebetween.

The first and second suction cup arms 130, 132 are preferably forced or brought together to form the closed U-shaped suction cup 118 (see FIG. 4) by cables 135 attached to each of the first and second suction cup arms 130, 132. Since the first and second suction cup arms 130, 132 are L-shaped, they have a fulcrum point 137 thereby the cables 135 can be attached to the short side 130a, 132a of the fulcrum point 137 in order to move the long side 130b, 132b as a surgeon applies a pulling force to the cables 135. With the desired layer of tissue folded and vacuumed within the space defined by the first and second suction cup members 130, 132, the needle 122 is advanced through the central portion of the suction cup 118 for penetrating only the desired layers of tissue 25.

Figure 5:
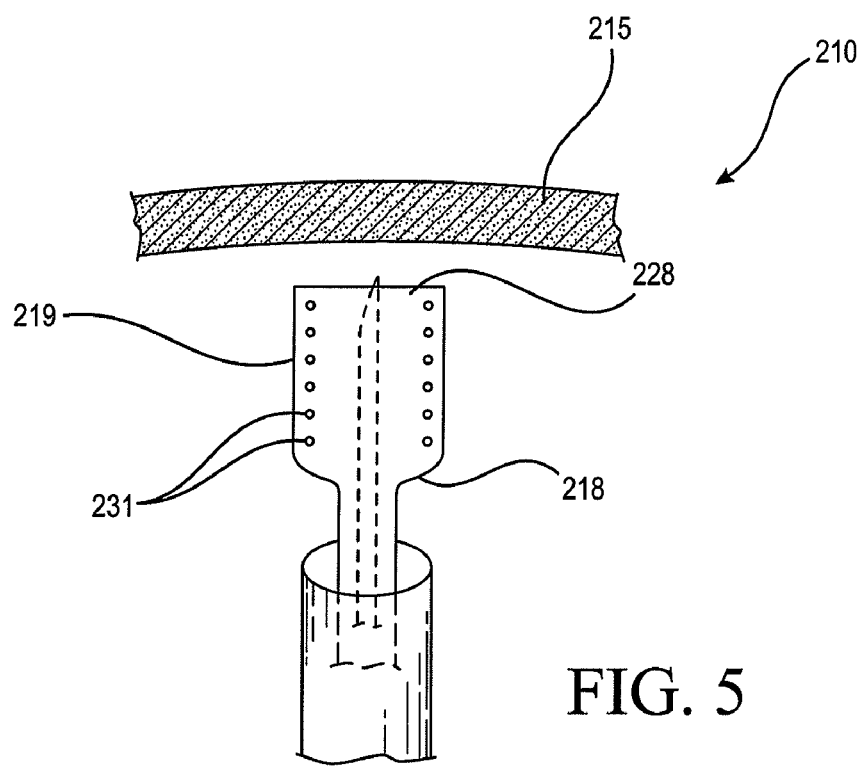
FIGS. 5 and 6 are cross sectional views of another embodiment of a tissue puncture assembly in use.
Figure 6:
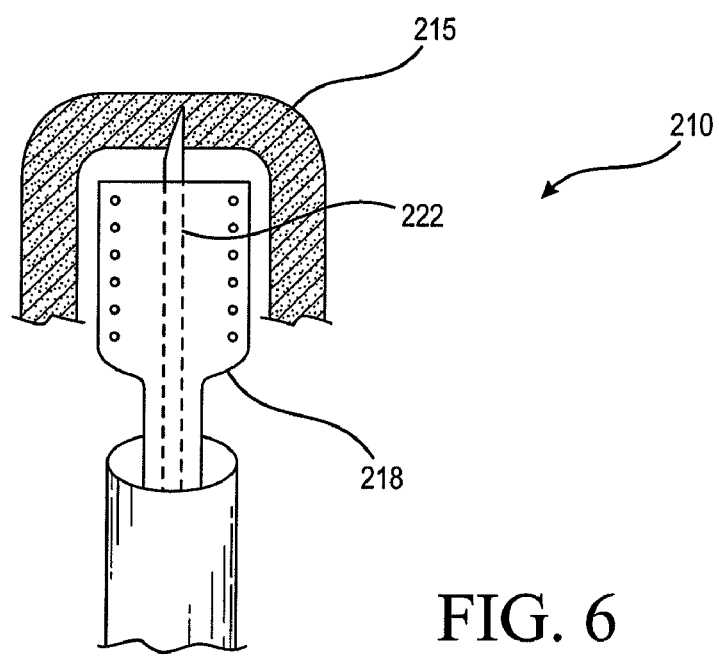

In accordance with yet a further embodiment as shown with reference to FIGS. 5 and 6, the tissue puncture assembly 210 once again includes a suction cup 218 and a needle 222 extending along a central section thereof. However, in this embodiment the suction ports 231 run along the outer surface 219 of suction cup 218 to draw tissue 215 thereabout. With the tissue 215 vacuumed to a position draping over the open end 228 of the suction cup 218, the needle 222 is advanced distally relative to the suction cup 218 such that it is able to penetrate tissue in a highly controlled manner.

In accordance with a preferred embodiment of the present invention, the fastening elements/fasteners are metal, plastic or other biocompatible materials determined to be appropriate for use in the practice of the present invention. Once the needle penetrations are formed in accordance with the present invention, these fasteners may be readily secured to the stomach tissue in a highly controlled manner as disclosed in commonly owned U.S. patent application Ser. No. 11/779,322, entitled "HYDRID ENDOSCOPIC/LAPAROSCOPIC METHOD FOR FORMING SEROSA TO SEROSA PLICATIONS IN A GASTRIC CAVITY", filed Jul. 18, 2007, which is incorporated herein by reference. In order to induce tissue overgrowth and thus reinforcement of the resulting tissue fold, a mesh or buttress material may be fastened between the stomach wall and the staple. This would have the net effect of distributing some of the loading over the mesh and ensuring that if one fastener were to come loose, the integrity of the entire line would not be compromised.

As those skilled in the art will certainly appreciate, the process of penetrating the tissue and applying fasteners is repeated at various predetermined stomach wall locations. In accordance with a preferred embodiment of the present invention, the fasteners are applied vertically along the stomach creating a fastener arrangement necessary to ultimately form a mattress stitch pattern. The exact direction in which the fasteners are applied is not critical and medical practitioners may apply the fasteners in a direction and order which best suits the specific patient. For example, the fasteners may be applied to the stomach wall alternating between the anterior and posterior wall of the stomach as the present tissue puncture assembly is moved distally to proximally.

Utilizing a deployment assembly, the fasteners, in conjunction with a suturing material are secured at the various sites. With the suture material strung between the anterior and posterior walls of the stomach at the locations previously treated in accordance with the present invention, the suture material may be pulled taut to bring the gastric wall into approximation with each other. Although a mattress stitch pattern is disclosed with a preferred embodiment of the present invention, other stitch patterns may be employed without departing from the spirit of the present invention.

The resulting structure of the stomach is that of a tubular member connecting the esophagus to the pylorus with the gastric remnant allowed to pass gastric acid into the food stream. This produces a smaller stomach pouch as well as a restrictive means for the bolus. In accordance with an alternate embodiment, the resulting structure may be that of a tubular member starting substantially at the esophagus and extending some distance from the pylorus.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that the device is sterilized. This can be done by any number of ways known to those skilled in the art including beta or gamma radiation, ethylene oxide, and/or steam.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A device for safely penetrating the tissue of a gastric wall comprising: a tissue puncture assembly including a suction device in the form of a cup with suction ports therein and an open distal end, the cup including a first suction cup arm and a second suction cup arm, the first suction cup arm and the second suction cup arm being pivotally mounted for movement between an open configuration and a closed configuration, wherein the first suction cup arm and the second suction cup arm constitute respective halves of the cup such that when brought together in the closed configuration the first suction cup arm and the second suction cup arm define a closed U-shaped cup with the open distal end; and a needle surrounded by the cup and extending through the cup toward the open distal end.

2. The device of claim 1, wherein each of the first suction cup arm and the second suction cup arm is L-shaped when viewed along a cross section.

3. The device of claim 1, wherein the first and second cup arms are mechanically pivoted and the device further includes a cable respectively secured to each of the first suction cup arm and the second suction cup arm, and each of the first suction cup arm and the second suction cup arm includes a fulcrum point such that when the cable is pulled upon at a short side of the fulcrum point the first suction cup arm and the second suction cup arm are moved to the closed configuration.

4. The device of claim 1, wherein the suction ports are on an inner surface of each of the first suction cup arm and the second suction cup arm such that tissue is drawn into the suction device.

5. The device of claim 1, wherein the needle is an RF needle.

6. The device of claim 1, wherein the needle is a Veress needle.

* * * * *